United States Patent [19]

Koumoto et al.

[11] Patent Number: 5,294,706
[45] Date of Patent: Mar. 15, 1994

[54] PROCESS FOR PREPARING 1,5-BENZOTHIAZEPINE DERIVATIVES

[75] Inventors: Tadayuki Koumoto, Osaka; Hironori Hayashi, Toyonaka; Toshiya Kadowaki, Osaka; Masahiko Seto, Kobe; Toyonari Oine, Nara, all of Japan

[73] Assignee: Tanabe Seiyaku Co., Ltd., Osaka, Japan

[21] Appl. No.: 979,417

[22] Filed: Nov. 19, 1992

Related U.S. Application Data

[63] Continuation of Ser. No. 659,663, Feb. 25, 1991, abandoned.

[30] Foreign Application Priority Data

Mar. 8, 1990 [JP] Japan .................... 2-57798

[51] Int. Cl.$^5$ .......................................... C07D 281/10
[52] U.S. Cl. ......................................................... 540/491
[58] Field of Search ........................................... 540/491

[56] References Cited

U.S. PATENT DOCUMENTS

| | | | |
|---|---|---|---|
| 3,562,257 | 2/1971 | Kugita et al. | 540/491 |
| 4,438,035 | 3/1984 | Gaino et al. | 540/491 |
| 4,474,956 | 10/1984 | Zirngibi et al. | 544/49 |
| 5,008,411 | 4/1981 | Coffen et al. | 540/491 |
| 5,013,835 | 5/1991 | Rossey et al. | 514/491 |
| 5,055,575 | 10/1991 | Nishimoto et al. | 540/491 |
| 5,102,998 | 4/1992 | Rossey et al. | 540/491 |
| 5,144,025 | 9/1992 | Tentorio | 540/491 |

FOREIGN PATENT DOCUMENTS

| | | | |
|---|---|---|---|
| 0098422 | 1/1984 | European Pat. Off. | 544/49 |
| 0343474 | 11/1989 | European Pat. Off. | 540/491 |
| 0378455 | 7/1990 | European Pat. Off. | 540/491 |
| 0392543 | 10/1990 | European Pat. Off. | 540/491 |
| 0395302 | 10/1990 | European Pat. Off. | 540/491 |
| 0395323 | 10/1990 | European Pat. Off. | 540/491 |
| 46-8982 | 3/1971 | Japan | 540/491 |
| 46-43785 | 12/1971 | Japan | 540/491 |
| 53-18038 | 6/1978 | Japan | 540/491 |

OTHER PUBLICATIONS

Kugita et al, "Synthesis of 1,5-Benzothiazepine Derivatives, I", Chem. Pharm. Bull., 18, 2028–2037 (1970).
Registry of Toxic Effects of Chemical Substances 1985-1986, pp 804 and 5121.
Handbook of Industrial Toxicology pp. 124–127.

Primary Examiner—Robert T. Bond
Attorney, Agent, or Firm—Browdy and Neimark

[57] ABSTRACT

There is disclosed a process for preparing 1,5-benzothiazepine derivatives of the formula:

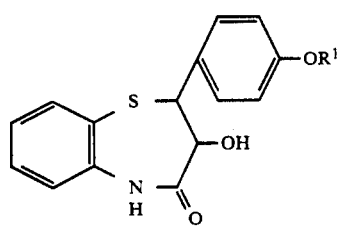

(I)

wherein $R^1$ is a lower alkyl group, or a salt thereof which comprises subjecting a propionate derivatives of the formula:

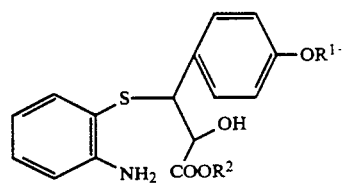

(II)

wherein $R^2$ is an ester residue and $R^1$ is the same as defined above, to intramolecular cyclization in the presence of a sulfonic acid compound of the formula:

$R^3SO_3H$ (III)

wherein $R^3$ is a lower alkyl group or a substituted or unsubstituted phenyl group, in a non-halogenated organic solvent and, if desired, converting the product to a salt thereof.

8 Claims, No Drawings

PROCESS FOR PREPARING 1,5-BENZOTHIAZEPINE DERIVATIVES

CROSS-REFERENCE TO RELATED APPLICATIONS

This application is a continuation of application Ser. No. 07/659,663, filed Feb. 25, 1991, the contents of which are hereby incorporated herein by reference now abandoned.

BACKGROUND OF THE INVENTION

This invention relates to a novel process for preparing 1,5-benzothiazepine derivatives of the formula:

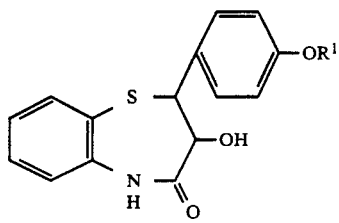

(I)

wherein $R^1$ is a lower alkyl group, or a salt thereof.

The above 2-(4-lower alkoxyphenyl)-3-hydroxy-2,3-dihydro-1,5-benzothiazepin-4(5H)-one is useful as an intermediate for the synthesis of medical compounds, for the example, (+)-cis-2-(4-methoxyphenyl)-3-acetoxy-5-($\beta$-dimethylaminoethyl)-2,3-dihydro-1,5-benzothiazepin-4(5H)-one (generic name: Diltiazem) which is excellent coronary vasodilator.

Heretofore, there have been known that said intermediate can be prepared by the two steps of, for example, hydrolyzing ethyl 2-hydroxy-3-(2-aminophenylthio)-3-(4-methoxyphenyl)propionate with alkali to give corresponding free acid and then subjecting it to intramolecular cyclization under heating (Japanese Patent Publication (examined) No. 8982/1971).

It is an object of the present invention to provide a novel process for preparing said intermediates from 2-hydroxy-3-(2-aminophenylthio)-3-(4-lower alkoxyphenyl)propionate in a high yield by one step.

DETAILED DESCRIPTION OF THE INVENTION

According to the present invention, 1,5-benzothiazepine derivatives of the formula (I) can be prepared by subjecting a propionate derivative of the formula:

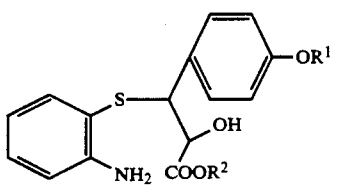

(II)

wherein $R^2$ is an ester residue and $R^1$ is the same as defined above, to intramolecular cyclization in the presence of a sulfonic acid compound of the formula:

$$R^3SO_3H \qquad (III)$$

wherein $R^3$ is a lower alkyl group or a substituted or unsubstituted phenyl group, in a non-halogenated organic solvent.

The ester residue represented by $R^2$ of the starting compound (II) may be any groups which are not concerned with the reaction, for example, a lower alkyl group.

Examples of the sulfonic acid compound (III) to be used in the intramolecular cyclization include, for example, the compound wherein $R^3$ of the formula (III) is an alkyl group having 1 to 4 carbon atoms such as methyl group, ethyl group, propyl group or butyl group or phenyl group which may be substituted by at least one of these alkyl groups. Among them, more preferred are methanesulfonic acid and p-toluenesulfonic acid. An amount of the sulfonic acid compound is not particularly limited but generally, it is preferably used at an amount of about 0.1 to 10 w/w %, more preferably about 0.5 to 6 w/w %, based on the compound (II).

The solvents used in the invention are not particularly limited and any of a non-halogenated organic solvent which will not hinder the reaction can be used. Examples of such solvents include a high boiling point solvent, for example, ethers such as n-propyl ether, n-butyl ether, isobutyl ether, n-pentyl ether or dioxane; non-halogenated aromatic solvents such as xylene, toluene, ethylbenzene, isobutylbenzene, isopropylbenzene, n-propylbenzene or anisole; aliphatic hydrocarbons such as n-pentan, n-ocotane or n-nonane.

It is especially preferred to use toluene, ethylbenzene or xylene. It is preferable to carry out intramolecular cyclization at 90° to 160° C. in the above mentioned solvent, especially 110° to 145° C. Since the above-mentioned reaction is carried out without racemization, the desired compound (I) in the optically active form can be obtained by using the optically active compound (II) as the starting material.

The desired compound (I) thus obtained can be converted to the corresponding 3-acetoxy-5-($\beta$-dimethylaminoethyl)-2,3-dihydro-1,5-benzothiazepine derivatives of the formula:

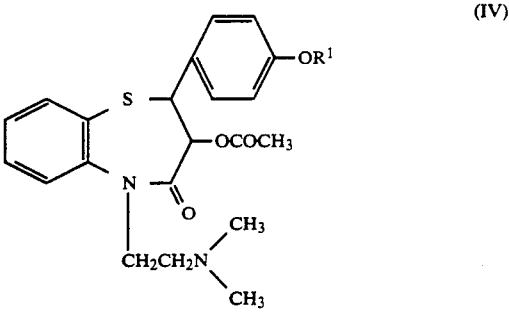

(IV)

wherein $R^1$ is the same as defined above, or a pharmaceutically acceptable salt thereof in a known method, for example, in a method described in Japanese Patent Publication (examined) Nos. 18038/1978 and 43785/1971 and U.S. Pat. Nos. 3,562,257 and 4,438,035, the contents of which are hereby incorporated herein by reference.

According to the process of the present invention, 1,5-benzothiazepine derivatives (I) can be obtained in a high yield of more than 85% by one step. Therefor, as compared with the known methods, the process of the invention is extremely excellent for the industrial process.

Further, when the starting compound (II) is prepared by reacting 2-aminothiophenol with 2,3-epoxy-3-(4-lower alkoxyphenyl) propionate in a non-halogenated organic solvent used in the invention, the reaction mixture can be subjected to the intramolecular cyclization without isolating said starting compound (II) from the mixture. In this case, the process of the present invention is advantageous for the industrial scale in that the desired compound (I) can be obtained from epoxy compounds by a substantially single reaction operation in a short time and a high yield.

When the intramolecular cyclization is carried out in the absence of the sulfonic acid compound (III) of the invention, a long time and a high temperature of 160° to 180° C. is required for the reaction and the yield of the desired compound is insufficient.

However, according to the process of the present invention, the reaction can be completed in a shorter time at a lower temperature as compared with the above case and the yield of the desired compound (I) is high.

Throughout the specification and Claims, the term "lower alkyl" and "lower alkoxy" are interpreted as the alkyl of 1 to 4 carbon atoms and alkoxy of 1 to 4 carbon atoms, respectively.

EXAMPLE 1

A mixture of 40 g of methyl (2R,3S)-2,3-epoxy-3-(4-methoxyphenyl)propionate, 26.5 g of 2-aminothiophenol and 300 ml of xylene is heated at 110° to 120° C. for 1 hour, whereby the reaction mixture containing methyl (2S,3S)-3-[(2-aminophenyl)thiol]-2-hydroxy-3-(4-methoxylphenyl)propionate is obtained. 380 mg of methanesulfonic acid are added to the mixture and the mixture is refluxed for 7 hours. During the reaction, methanol formed is removed by the azeotropic distillation with xylene. The mixture is cooled to under 10° C. and then stirred for 1 hour. Precipitated crystals are collected by filtration, washed with cooled methanol and then dried, whereby 49.1 g of (2S,3S)-3-hydroxy-2-(4-methoxyphenyl)-2,3-dihydro-1,5-benzothiazepin-4(5H)-one are obtained. Yield: 84.8% m.p.: 204°-205° C. [α]$_D^{20}$+115° (c=0.5, dimethylformamide)

EXAMPLE 2

A mixture of 40 g of methyl (2R,3S)-2,3-epoxy-3-(4-methoxyphenyl)propionate, 26.5 g of 2-aminothiophenol and 300 ml of toluene is heated at 110° to 115° C. for 1 hour, whereby the reaction mixture containing methyl (2S,3S)-3-[(2-aminophenyl)thio]-2-hydroxy-3-(4-methoxylphenyl)propionate is obtained. After cooled to 80° to 90° C., 1.5 g of methanesulfonic acid are added to the mixture and the mixture is refluxed for 18 hours. During the reaction, methanol formed is removed by the azeotropic distillation with toluene. Then the mixture is treated in the same manner as described in Example 1, whereby 46.9 g of (2S,3S)-3-hydroxy-2-(4-methoxyphenyl)-2,3-dihydro-1,5-benzeothiazepine-4(5H)-one are obtained. Yield: 81.0% m.p.: 203°-204° C. [α]$_D^{20}$+115° (c=0.5, dimethylformamide)

EXAMPLE 3

A mixture of 40 g of methyl (2R,3S)-2,3-epoxy-3-(4-methoxyphenyl)propionate, 26.5 g of 2-aminothiophenol and 250 ml of xylene is heated at 110° to 120° C. for 1 hour, whereby the reaction mixture containing methyl (2S,3S)-3-[(2-aminophenyl)thio]-2-hydroxy-3-(4-methoxylphenyl)propionate is obtained. 600 mg of p-toluenesulfonic acid hydrate are added to the mixture and the mixture is refluxed for 8 hours. During the reaction, methanol formed is removed by the azeotropic distillation with xylene. Then the mixture is treated in the same manner as described in Example 1, whereby 47.5 g of (2S,3S)-3-hydroxy-2-(4-methoxyphenyl)-2,3-dihydro-1,5-benzothiazepin-4(5H)-one are obtained. Yield: 82.1% m.p.: 203°-204° C. [α]$_D^{20}$+115° (c=0.5, dimethylformamide)

We claim:

1. A process for preparing 1,5-benzothiazepine derivatives of the formula:

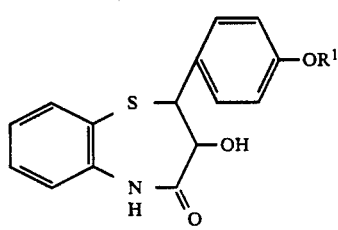

(I)

wherein R$^1$ is a lower alkyl group, or a salt thereof which comprises subjecting a propionate derivative of the formula:

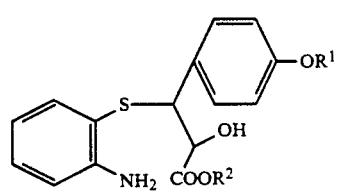

(II)

wherein R$^2$ is a lower alkyl group and R$^1$ is the same as defined above, to intramolecular cyclization in the presence of a sulfonic acid compound of the formula:

R$^3$SO$_3$H    (III)

wherein R$^3$ is a lower alkyl group or a substituted or unsubstituted phenyl group, in a non-halogenated aromatic solvent and, optionally converting the product to a salt thereof.

2. A process according to claim 1, wherein R$^3$ of the formula (III) is a methyl group, an ethyl group, a propyl group, or a phenyl group which is optionally substituted by at least one moiety selected from the group consisting of a methyl group, an ethyl group, a propyl group and a butyl group.

3. A process according to claim 2, wherein the sulfonic acid compound (III) is methanesulfonic acid or p-toluenesufonic acid.

4. A process according to claim 3, wherein the non-halogenated aromatic solvent is xylene, toluene, ethylbenzene, isobutylbenzene, isopropylbenzene, n-propylbenzene or anisole.

5. A process according to claim 4, wherein the non-halogenated aromatic solvent is xylene or toluene.

6. A process according to claim 1, wherein the sufonic acid (III) is used at an amount of 0.1 to 10 w/w % based on the compound (II).

7. A process according to claim 6, wherein the sufonic acid (III) is used at an amount of 0.5 to 6 w/w % based on the compound (II).

8. A process for preparing 3-acetoxy-5-(β-dimethylaminoethyl)-2,3-dihydro-1,5-benzothiazepine derivatives of the formula:

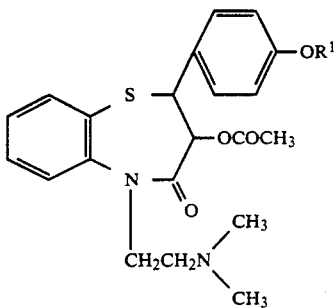
(IV)

wherein R¹ is a lower alkyl group, or a pharmaceutically acceptable salt thereof, which comprises the steps of:

a) subjecting a propionate derivative of the formula:

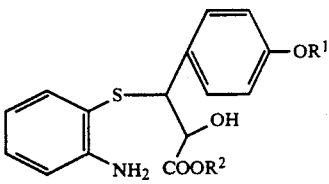
(II)

wherein R² is a lower alkyl group and R¹ is the same as defined above, to intramolecular cyclization in the presence of a sulfonic acid compound of the formula:

$$R^3SO_3H \quad (III)$$

wherein R³ is a lower alkyl group or a substituted or unsubstituted phenyl group, in a non-halogenated aromatic solvent to give a 1,5-benzothiazepine derivative of the formula:

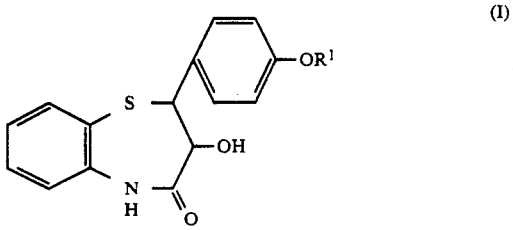
(I)

wherein R¹ is the same as defined above, and
b) converting the compound (I) to the corresponding 3-acetoxy-5-(β-dimethylaminoethyl)-1,5-benzothiazepine derivative or a pharmaceutically acceptable salt thereof.

* * * * *